(12) United States Patent
Haverlah et al.

(10) Patent No.: US 11,341,267 B1
(45) Date of Patent: May 24, 2022

(54) DEATH CERTIFICATE INFORMATION PROCESSING TECHNIQUES

(71) Applicant: United Services Automobile Association (USAA), San Antonio, TX (US)

(72) Inventors: Sharon Kay Haverlah, Bulverde, TX (US); Alexander Benetto Nagelberg, San Antonio, TX (US)

(73) Assignee: United Services Automobile Association (USAA), San Antonio, TX (US)

( * ) Notice: Subject to any disclaimer, the term of this patent is extended or adjusted under 35 U.S.C. 154(b) by 283 days.

(21) Appl. No.: 16/545,818

(22) Filed: Aug. 20, 2019

Related U.S. Application Data

(60) Provisional application No. 62/719,878, filed on Aug. 20, 2018.

(51) Int. Cl.
| | |
|---|---|
| *G06F 21/62* | (2013.01) |
| *G16H 10/60* | (2018.01) |
| *H04L 9/32* | (2006.01) |
| *H04L 9/06* | (2006.01) |

(52) U.S. Cl.
CPC ........ *G06F 21/6245* (2013.01); *G16H 10/60* (2018.01); *H04L 9/0637* (2013.01); *H04L 9/3247* (2013.01); *H04L 2209/38* (2013.01)

(58) Field of Classification Search
CPC . G06F 21/6245; H04L 9/3247; H04L 9/0637; H04L 2209/38; G16H 10/60
See application file for complete search history.

(56) References Cited

U.S. PATENT DOCUMENTS

| | | | |
|---|---|---|---|
| 10,733,616 B1 * | 8/2020 | Rutley | G06Q 30/018 |
| 2017/0046664 A1 * | 2/2017 | Haldenby | H04L 63/0876 |
| 2018/0039942 A1 * | 2/2018 | Rogers | H04L 67/22 |
| 2018/0117446 A1 * | 5/2018 | Tran | A42B 3/0433 |
| 2019/0166133 A1 * | 5/2019 | Frederick | H04L 63/12 |

* cited by examiner

*Primary Examiner* — Harunur Rashid
(74) *Attorney, Agent, or Firm* — Fletcher Yoder, P.C.

(57) ABSTRACT

A system includes at least one processor and at least one memory communicatively coupled to the at least one processor, where the at least one memory stores instructions. When executed by the at least one processor, the instructions are configured to receive death certificate information from a node of a distributed ledger system, determine, a record to be updated based at least in part on the death certificate information, and update the record. The death certificate information and the record are associated with an individual.

19 Claims, 4 Drawing Sheets

DEATH CERTIFICATE INFORMATION PROCESSING TECHNIQUES

CROSS REFERENCE TO RELATED APPLICATIONS

This application claims priority from and the benefit of U.S. Provisional Application Ser. No. 62/719,878, entitled "DEATH CERTIFICATE INFORMATION PROCESSING TECHNIQUES," filed Aug. 20, 2018, which is hereby incorporated by reference in its entirety for all purposes.

BACKGROUND

The present disclosure relates to processing and maintenance of medical records. More specifically, the present disclosure relates to systems and methods for receiving information related to death certificates and updating records of an individual based on the information.

Certain records, such as electronic medical records, may include sensitive information related to an individual. As an example, medical records may include sensitive information associated with an individual, such as information identifying the individual, a medical history of the individual, health insurance information associated with the individual, and/or the like. Accordingly, regulatory requirements, such as the Health Insurance Portability and Accountability Act of 1996 (HIPAA), may provide specific instructions regarding the use of the electronic records. As a result, modifying and/or updating medical records may be cumbersome. For example, medical information, such as information on a death certificate, may be verified and confirmed prior to being incorporated into a medical record. In some instances, verification may depend on processing of several documents via one or more governmental entities, such as the issuing of death certificates. Thus, the verification process may increase an amount of time to update and process information associated with death certificates.

BRIEF DESCRIPTION

Certain embodiments commensurate in scope with the originally claimed subject matter are summarized below. These embodiments are not intended to limit the scope of the disclosure, but rather these embodiments are intended only to provide a brief summary of certain disclosed embodiments. Indeed, the present disclosure may encompass a variety of forms that may be similar to or different from the embodiments set forth below.

In one embodiment, a system includes at least one processor and at least one memory communicatively coupled to the at least one processor, where the at least one memory stores instructions. When executed by the at least one processor, the instructions are configured to receive death certificate information from a node of a distributed ledger system, determine, a record to be updated based at least in part on the death certificate information, and update the record. The death certificate information and the record are associated with an individual.

In another embodiment, a system includes a node of a plurality of nodes of a distributed ledger system, where the node includes at least one processor and at least one memory communicatively coupled to the at least one processor, where the at least one memory stores instructions. When executed by the at least one processor, the instructions are configured to receive death certificate information from another node of the plurality of nodes, verify that the death certificate information is valid based at least in part on verification data of the death certificate information, access a record associated with an individual upon verifying that the death certificate information is valid, and adjust the record based at least in part on the death certificate information.

In another embodiment, a system includes at least one processor and at least one memory communicatively coupled to the at least one processor, where the at least one memory stores instructions. When executed by the at least one processor, the instructions are configured to receive a blockchain that includes death certificate information, identify that the death certificate information is associated with an individual, append the blockchain upon identifying that the death certificate information is associated with the individual to generate an appended blockchain, and determine a record to be updated based at least in part on the death certificate information, where the record is associated with the individual.

Various refinements of the features noted above may exist in relation to various aspects of the present disclosure. Further features may also be incorporated in these various aspects as well. These refinements and additional features may exist individually or in any combination. For instance, various features discussed below in relation to one or more of the illustrated embodiments may be incorporated into any of the above-described aspects of the present disclosure alone or in any combination. The brief summary presented above is intended only to familiarize the reader with certain aspects and contexts of embodiments of the present disclosure without limitation to the claimed subject matter.

BRIEF DESCRIPTION OF THE DRAWINGS

These and other features, aspects, and advantages of the present disclosure will become better understood when the following detailed description is read with reference to the accompanying drawings in which like characters represent like parts throughout the drawings, wherein.

DETAILED DESCRIPTION

Figure 1:
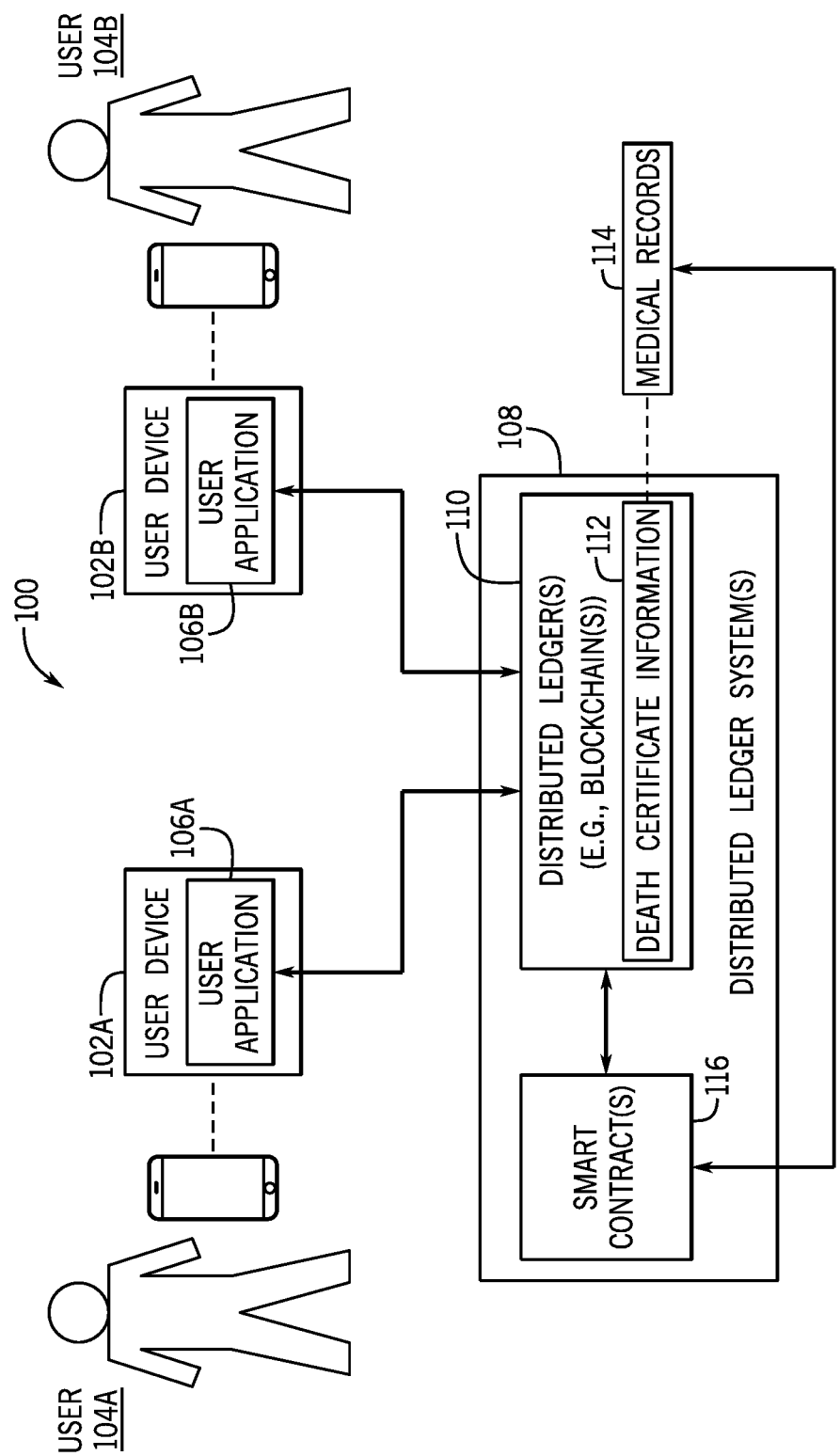
FIG. 1 illustrates a block diagram of a system for managing information using a distributed ledger, in accordance with embodiments described herein.

One or more specific embodiments will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

The present disclosure relates to death certificate information processing. Embodiments of the present disclosure utilize blockchain and distributed ledger techniques as a shared infrastructure that connects all the parties involved (e.g., records owner(s) and various authoritative entities, such as notary public, the state department, foreign consulates/embassies, and so forth), and utilize the immutable nature of the distributed ledger to track the authentication certification history of electronic information, with a verifiable identity of each certifying entity in the chain of the death certificate. Using the embodiments described here, the entire certification history of each piece of electronic information may be tracked and verified on the blockchain/distributed ledger. Doing so, among other things, reduces the time to acquire authentication certification from multiple authorities from days or weeks down to minutes, saves cost of mailing and fees for representative services, eliminates the risk of important documents getting lost, and reduces fraud risks.

Embodiments of the present disclosure provide many other advantages. Because the embodiments described herein employ distributed ledgers (e.g., blockchains) to store and publish information regarding death certificate information, the death certificate information data is immutable and less prone to fraud, destruction, or corruption compared to storage on traditional storage systems. Accordingly, the embodiments described herein avoid the expenditure of processing, memory, storage, networking, and/or other computational resources that may be used when traditional systems attempt to restore information that has been lost or corrupted. Similarly, by providing a more secure and reliable mechanism for managing certified information, the embodiments described herein avoid the expenditure of computing resources that may be used when traditional systems are required to back out or otherwise reverse fraudulent or erroneously performed information entry. Moreover, through the utilization of smart contracts and/or side chains, certain embodiments significantly increase the speed at which transactions occur, compared to traditional systems. The embodiments described herein also increase the speed of transfer processing by related components and/or systems, such as title search systems, legal support systems, systems of government agencies (e.g., building agencies, title registrars, etc.), and so forth. Moreover, by managing records through distributed ledger system(s), the embodiments described herein provide superior electronic provenance compared to human operated systems.

Embodiments of the present disclosure are directed to systems, devices, methods, and computer-readable media for managing certification of certain information (e.g., death certificate information) using information stored on a distributed ledger (e.g., a blockchain). The embodiments described herein employ a distributed ledger, such as a blockchain, to securely store data describing, for example, the current possessor(s) of the information, the previous possessor (s) of the information, the history of transfers of the information, accuracy of the information, and/or other aspects regarding the information. Use of a distributed ledger may provide an immutable, readily auditable record of the "chain of custody" of the information. In certain embodiments, the information is a physical (e.g., tangible) document, but in other embodiments, the information may be an electronic document.

The embodiments described herein provide improved systems and methods for processing information related to death certificates. More specifically, certain embodiments are directed to transferring and verifying death certificate information via a distributed ledger. As the death certificate information may include sensitive information related to an individual, such as a medical history of the individual and/or information associated with others related to the individual, the access by one or more entities may be restricted based on one or more factors. Thus, the death certificate information may be encrypted and access to the death certificate information, such as to verify and/or modify the death certificate information, may be selectively permitted based on a computing device of certain trusted entities. In some embodiments, the distributed ledger is public and any person of the general public may transfer (e.g., append) death certificate information to the distributed ledger, where the death certificate information is verified by trusted entities (e.g., physicians, healthcare providers, health insurance companies). In additional or alternative embodiments, the distributed ledger is private and only trusted entities may transfer and/or verify death certificate information.

In certain embodiments, the distributed ledger may be accessed to manage certain transactions based on the death certificate information. For example, after the death certificate information has been verified, a medical record may be updated and/or certain actions associated with the medical updates may be completed (e.g., transfer of assets). In certain traditional systems, such transactions may be executed after processing certain documents. As a result, creating such documents may delay the execution of the transactions, despite a completion of other steps in verification process.

Accordingly, the present disclosure provides techniques to facilitate the verifying of death certificate information. For example, by permitting certain portions of the death certificate information to be verified by certain trusted entities, the time used to await the processing of documents may be reduced. As a result, medical records may be updated more efficiently and transactions (e.g., providing information to estates, creditors, insurance companies, funeral homes) related to the updated medical records may be executed more effectively. Additionally, by permitting access to the death certificate information to trusted entities and to permit modification of medical records after verification by the trusted entities, the death certificate information may be confirmed more accurately and/or more securely. Thus, at least in some instances, the techniques described herein may protect the data records stored in the distributed file system from corruption, unauthorized use, and/or erroneous modification.

In general, the embodiments described herein utilize blockchain and distributed ledger techniques, as well as smart contracts in certain embodiments, to transfer, distribute, and/or verify death certificate information.

FIG. 1 illustrates a block diagram of a system 100 for managing information using a distributed ledger, in accordance with embodiments described herein. As illustrated in FIG. 1, the system may include one or more user devices 102 that are each owned by, operated by, or otherwise associated with a user 104. As used herein, a user may refer to any entity who is permitted to interact with transactions and/or information associated with the distributed ledger. Thus, each user 104 may be a single user 104, a group of users 104, a corporation, an organization, some other entity, or any combination thereof. In some instances, the user 104 may be a Decentralized Autonomous Organizations (DAO) including one or more autonomous artificial intelligence (AI) agents that perform operations and make decisions regarding the transactions and/or information. The user device(s) 102 may include any appropriate type of computing device, such as portable device(s) (e.g., smartphones, tablet computers, wearable computers, etc.) and less mobile device(s) (e.g., desktop computers). A user device 102 may execute a user application 106 that enables the user 104 to distribute, access, and/or modify death certificate information 112 stored on one or more distributed ledgers 110. The distributed ledger(s) 110 may be implemented on one or more distributed ledger systems 108. The distributed ledger system(s) 108 may include any appropriate type and number of user device(s) 102, such as server computer(s) and/or distributed computing device(s) (e.g., cloud server(s)). The distributed ledger system(s) 108 may communicate with the user device(s) 102 and/or other computing device(s) over one or more networks.

Each user 104 of the system 100 may be an append-only, a read-only, or a read and append type user. As an example, the user 104A is a healthcare provider that may own and/or control death certificate information 112 associated with medical records 114, which may or may not be stored in the distributed ledger(s) 110. The medical records 114 may include, for example, information related to an individual, such as a patient of the healthcare provider. The information may include identification information (e.g., a name, a social security number, and/or the like), health insurance information, medical data (e.g., medical image data, laboratory data), a medical history of the patient, and/or any other data that may be relevant to the patient. The user 104A may be permitted to append (e.g., modify and/or add) death certificate information 112 of the medical records 114. In other words, the user 104A is permitted to append the death certificate information 112. The user 104A may also be permitted to access death certificate information 112 appended by another user 104. That is, the user 104A is permitted to read the death certificate information 112. By reading the death certificate information 112, the user 104A may then verify that the death certificate information 112 is accurate. Thus, the user 104A is capable of both reading and appending death certificate information 112. On the other hand, a user 104B may be capable of reading the death certificate information 112 or appending the death certificate information 112, but not both. By way of example, if the user 104B is append-only, the user 104B may append death certificate information 112, but is not permitted to verify the death certificate information 112 appended by other users 104. If the user 104B is read-only, the user 104B may access death certificate information 112 the death certificate information 112 appended by other users 104, but is not permitted to modify and/or add death certificate information 112.

In some embodiments, the death certificate information 112 may update particular medical records 114. That is, if death certificate information 112 is appended, certain changes are made to medical records 114 associated with individuals of which the death certificate information 112 is relevant to. For example, information associated with a cause of death may be added to the medical records 114. It should also be understood that in some cases, a modification of the medical records 114 may result in a modification of death certificate information 112. In one example, the medical records 114 may be updated to include information from a hospital, such as billing information and/or patient information, and a notification indicative of possible death certificate information 112 may be appended. As a result, death certificate information 112 may be appended within the distributed ledger(s) 110 from the updated medical records 114. Additionally, in certain embodiments, the distributed ledger system(s) 108 may execute one or more smart contracts 116 stored on the distributed ledger(s) 110. The smart contract(s) 116 may include executable logic that further updates the medical records 114. Updates may be made by writing transaction(s) to the append-only structure of the distributed ledger(s) 110. In certain embodiments, the smart contract(s) 116 may apply logic, e.g., according to one or more rules, to append death certificate information 112. For example, the medical records 114 associated with a first individual may update to reflect the verified death certificate information 112. As a result of the update, a smart contract 116 is executed to update the medical records 114 associated with a second individual. It should also be understood that in some embodiments, smart contract(s) 116 may also append death certificate information 112. For example, death certificate information 112 appended for a first individual may also trigger a smart contract 116 to execute to append death certificate information 112 of a second individual.

In certain embodiments, the distributed ledger system 108 includes distributed ledger(s) 110 that are one or more blockchains, which can include a transaction database shared by all nodes participating in a system based on a predefined protocol (e.g., the BitCoin™ protocol). As used herein, a "node" may refer to any combination and/or collection of users 104, user devices 102, and/or user applications 106 that may act upon a blockchain system (e.g., verify and/or append transactions). In certain embodiments, the blockchain is a private blockchain (e.g., available to one or more entities/users that are credentialed users on a network). For example, each medical record 114 may be associated with its own distributed ledger 110 that includes death certificate information 112 related to the corresponding medical record 114. Additionally, any of the trusted entities may append death certificate information 112 to the distributed ledger 110. After death certificate information 112 is appended, any of the remaining trusted entities may view the death certificate information 112 and/or the medical record 114 in full (e.g., information associated with the time of death, cause of death). If the trusted entities verify the death certificate information 112 after viewing, the medical records 114 may update. In additional or alternative embodiments, the blockchain is a public permissioned blockchain (e.g., available to any and every entity/user on a network such as the internet). That is, in the public permissioned distributed ledger 110, any member of the public may append death certificate information 112 to the distributed ledger 110. However, certain portions of the death certificate information 112 and medical records 114 may be limited to particular entities (e.g., trusted entities). Other entities may view information such as identifiers to reference the death certificate information 112 and/or the medical records 114, but may not fully view the death certificate information 112 and/or the medical records 114. In some instances, such entities may be permitted to fully view the death certificate information 112 and/or the medical records 114 after obtaining permission from one or more trusted entities.

In any case, by storing and publishing the death certificate information 112 on a distributed ledger 110 (e.g., blockchain) that is secure, such that the death certificate information 112 may be appended but not deleted from the distributed ledger 110, certain embodiments may ensure that the document information is not corrupted or fraudulent. Moreover, by storing the death certificate information 112 on a distributed ledger 110 that is distributed across multiple distributed ledger system(s) 108, certain embodiments may reduce or eliminate the chance that the death certificate information 112 may be irrecoverably lost or destroyed, either intentionally or unintentionally during a natural disaster, fire, war, or other catastrophic event. As such, the distributed ledger(s) 110 may provide security, traceability, and/or metadata to be used to settle challenges against, for example, the authentication certification for a particular document. The distributed ledger system also provides immutability, such that data records written to the distributed ledger may not be changed or removed once written.

To provide further context for the present disclosure, a high-level discussion of blockchain technology is provided. In general, a blockchain is a public ledger of all transactions that have ever been executed in one or more contexts (e.g., new death certificate information 112 submitted). A blockchain grows as completed blocks are added with a new set of transactions. In some examples, a single block is provided from multiple transactions (e.g., multiple death certificate information 112 appended by different people). In general, blocks are added to the blockchain in a linear, chronological order by one or more computing devices in a peer-to-peer network of interconnected computing devices that execute a blockchain protocol. In short, the peer-to-peer network can be described as a plurality of interconnected nodes, each node capable of verifying and/or relaying transactions. Each node within the peer-to-peer network may maintain a copy of the blockchain, which is automatically downloaded to the node upon joining the peer-to-peer network. The blockchain protocol provides a secure and reliable method of updating the blockchain, copies of which are distributed across the peer-to-peer network, without use of a central authority.

Because nodes (e.g., healthcare providers, government entities) that are capable of verifying transactions need to know all previous transactions to verify a requested transaction, the nodes agree on which transactions have actually occurred, and in which order. For example, should two nodes observe different transaction histories, they will be unable to come to the same conclusion regarding the validity of a transaction. The blockchain techniques described herein enable all nodes to come to an agreement as to transactions that have already occurred, and in which order. As described in further detail below, a ledger of transactions for a tracked asset is agreed to based on the amount of work (e.g., computing work such as hashing) required to add a transaction to the ledger of transactions (e.g., add a block to the blockchain). Blockchains may also employ other protocols, for example, that may define "work" differently. The work may be a computing task that may be difficult for any single node (e.g., computing device) in the peer-to-peer network to complete quickly, but is relatively easy for any node (e.g., computing device) to verify.

In certain embodiments, the network may include a private blockchain wherein only users who are authorized to interact with the blockchain are allowed to do so. However, in other embodiments, the peer-to-peer network may include "miners" (e.g., computing devices) that add blocks to a blockchain based on the blockchain protocol. In general, multiple miners verify transactions that are to be added to a block, and compete (e.g., perform work, as described above) to have their block added to the blockchain. Verification of transactions includes verifying digital signatures associated with respective transactions. For a block to be added to the blockchain, a miner must demonstrate a proof of work before their proposed block of transactions is accepted by the peer-to-peer network, and is added to the blockchain. A blockchain protocol includes a proof of work scheme that is based on a cryptographic hash function (CHF). An example CHF includes the secure hash algorithm 256 (SHA-256). In general, the CHF receives information as input, and provides a hash value as output, the hash value being of a predetermined length. For example, SHA-256 outputs a 256-bit (32-byte, 64-character) hash value. In some examples, the hash value is a one-way hash value, in that the hash value cannot be 'un-hashed' to determine what the input was. The blockchain protocol can require multiple pieces of information as input to the CHF. For example, the input to the CHF can include a reference to the previous (most recent) block in the blockchain, details of the transaction(s) that are to be included in the block to be created, and a "nonce value" (e.g., a random number used only once).

Multiple nodes may compete to hash a set of transactions and to provide the next block that is to be added to the blockchain. The blockchain protocol provides a threshold hash to qualify a block to be added to the blockchain. For example, the threshold hash can include a predefined number of zeros (0's) that the hash value must have at the beginning (e.g., at least the first four characters of the hash value must each be zero). The higher the number of zeros, the more computationally time-consuming it may be to arrive at a qualifying hash value.

In accordance with the blockchain protocol, each miner in the peer-to-peer network receives transaction information for one or more transactions that are to be included in a block that is to be added next in the blockchain. Each miner provides the reference to the previous (most recent) block in the blockchain, details of the transaction(s) that are to be included in the block to be created block, and the nonce value to the CHF to provide a hash value. If the hash value does not meet the threshold hash (e.g., the first four characters of the hash value are not each zero), the miner starts again to provide another hash value. If the hash value meets the threshold hash (e.g., at least the first four characters of the hash value are each zero), the respective miner successfully created the next block that is to be added to the blockchain. Consequently, the respective miner's block is broadcast across the peer-to-peer network. All other miners cease work (because one miner was already successful), and all copies of the blockchain are updated across the peer-to-peer network to append the block to the blockchain. Each miner may be required to produce hundreds or thousands of hash values, before any one miner provides a qualifying hash value (e.g., at least the first four characters of the hash value are each zero).

In some cases, the distributed ledger system can include one or more sidechains. A sidechain can be described as a blockchain that verifies data from other blockchains. In some examples, a sidechain enables ledger objects (e.g., a digital currency) to be transferred between multiple blockchains. The blockchain may be a public blockchain, such that data stored on the blockchain is generally accessible. The blockchain or portions of the blockchain may alternatively or additionally be a private blockchain, such that the stored data is accessible only to authorized individuals and/or processes on the blockchain. By providing for tracked assets via blockchains, as further described below, enhanced transactional efficiencies, security, and smart contracts may be provided.

In certain embodiments, each node of the blockchain of the distributed ledger(s) 110 may access the death certificate information 112 with appropriate digital security tokens. The use of a distributed ledger 110 (e.g., a blockchain) to store the document data 112 may provide further security due to the characteristics of the distributed ledger 110. For example, the distributed ledger 110 may provide (e.g., built-in) security to ensure access is only granted to those users 104 with approved addresses and/or digital security tokens. The death certificate information 112 may be stored in a (e.g., unique) record on the distributed ledger 110, and such a record may be verifiable by multiple sources. The distributed nature of the distributed ledger(s) 110 may block the death certificate information 112 from being inadvertently or deliberately destroyed.

Within the distributed ledger(s) 110, a user 104A may seek to distribute the death certificate information 112 to another user 104B. In such an instance, the user 104A may access the distributed ledger 110 for the document and grant permission of access to the user 104B. Accordingly, the death certificate information 112 published by the distributed ledger 110 may provide confirmation that the chain of custody is sound, without gaps or inconsistencies. In some embodiments, a user 104 may access a reference (e.g., pointer) to the death certificate information 112. As such, the user 104 may not access raw data associated death certificate information 112 and as a result, the number of copies of the raw data may be limited. In this manner, the user 104 may be blocked from distributing additional copies of the electronic medical records to, for example, a computing device lacking permissions to access the electronic medical records. In certain embodiments, the smart contract(s) 116 may automatically perform operations according to preprogrammed rules that govern the distribution of death certificate information 112, for example, between a predetermined set of multiple trusted entities.

Each of the user(s) 104 may have a digital security token that is useable to request access and/or updates to the death certificate information 112 published by the distributed ledger(s) 110. In certain embodiments, the digital security token may be a cryptographic key (e.g., a private key) that is unique to a user 104. One or more private keys may be issued to one or more users 104 who enable their access to the distributed ledger 110. The private key(s) may each be associated with a public key corresponding to a particular distributed ledger 110, and each of the private keys may be employed with the public key to gain access to the distributed ledger 110. In certain embodiments, other credential(s) may also be used to control access to the distributed ledger(s) 110. For example, a user 104 may login to the user application 106 using a username, password, personal identification number (PIN), and/or other credentials. The private key of the user 104 may be stored on the user device 102, and the private key may be employed by the user application 106 to access the distributed ledger(s) 110 through a private-public key verification handshake. In certain embodiments, a federated identity model may be supported. The federated identity model may enable a user's identity to be verified based on the certification of an authority such as a healthcare provider. In such embodiments, a user 104 may request access to the distributed ledger 110 for a document, and the authority may confirm that the digital security token (e.g., key) supplied by the user 104 corresponds with the previously established identity of the user 104. Indeed, other data may be employed to authenticate the user 104. Such other data may be unique to the user 104. For example, the user 104 may be authenticated based at least partly on biometric data such as fingerprints, retinal maps, brainwave patterns, and so forth. In such instances, the biometric data may be collected using sensor device(s) that are in proximity to the user 104 and that are known to be trusted (e.g., secured against spoofing or other compromise). In general, certain embodiments support authentication of the user(s) 104 using any suitable number of authentication factors including but not limited to cryptographic keys or other digital security tokens, other credentials (e.g., username, password, PIN, challenge questions, etc.), biometric data, location information, and so forth.

Figure 2:
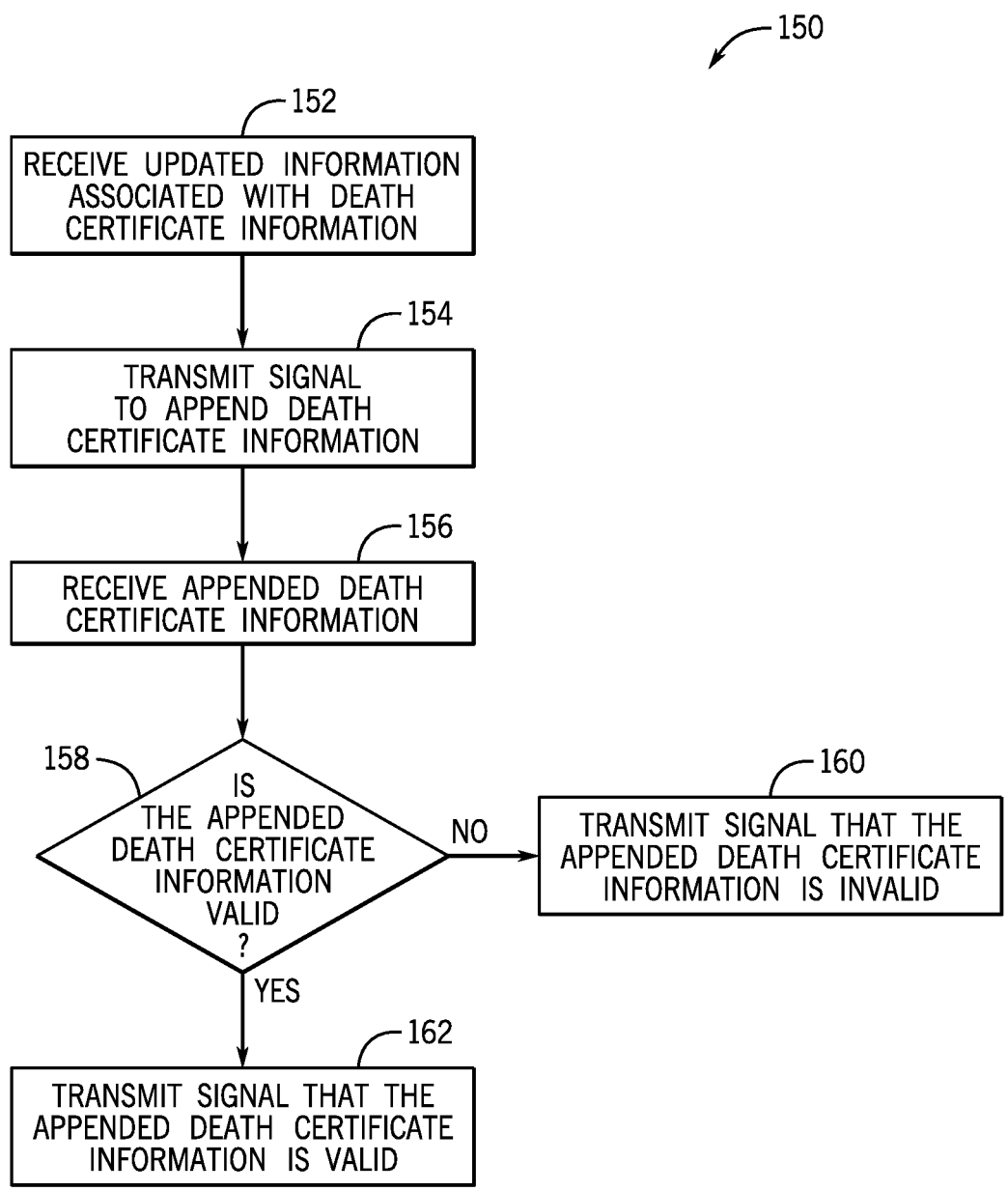
FIG. 2 illustrates a flowchart of a method of acting upon death certificate information using nodes of a distributed ledger, in accordance with embodiments described herein.

A description of a possible functions for nodes of the distributed ledger 110 is illustrated in FIG. 2, which is a flowchart of a method 150 that nodes may perform for the death certificate information 112. As mentioned, a node may include any user 104, any user device 102, any user application 106, or any combination thereof that is configured to act on a transaction (e.g., death certificate information 112) within the distributed ledger. In block 152, the node may receive updated information associated with the death certificate information 112. The updated information may be received external to the distributed ledger 110. As an example, the node may be a healthcare provider and receive updated information from an individual (e.g., a patient) associated with the healthcare provider.

Upon receiving updated information, the node may transmit a signal to the distributed ledger 110 to append the death certificate information 112 with the updated information, as indicated in block 154. The signal may include information associated with the appended death certificate information 112, including verification data (e.g., digital signatures) to enable other nodes of the distributed ledger 110 to verify the appended death certificate information 112. For example, the node may desire to update the medical records 114 with the information. To enable the medical records 114 to include the updated information, the node may append the death certificate information 112 in a form of a transaction, which then is uploaded to the distributed ledger 110. When the transaction is uploaded, other nodes of the distributed ledger 110 may verify the appended death certificate information such that the updated information is incorporated in the medical records 114.

In block 156, another node of the distributed ledger 110 may receive the appended death certificate information 112. Specifically, the appended death certificate information 112 may be distributed to other nodes capable of reading and verifying information of the distributed ledger 110. In some embodiments, different nodes may receive different portions of the appended death certificate information 112. That is, the appended death certificate information 112 may include a plurality of data and each node may receive a respective portion of the plurality of data to be verified. For example, a first node may receive a portion of a first verification data associated with a first individual. A second node may receive a remaining portion of the first verification data associated with the first individual. A third node may receive a second verification data associated with a second individual. It should be appreciated that in some embodiments, certain portions of data may be verified by more than one node. That is, a first node may receive a first verification data, a second node may receive a second verification data, and a third mode may receive the first verification data as well.

At block 158, the node determine if the appended death certificate information 112 is valid. In some embodiments, the appended death certificate information 112 may be verified via verifying digital signatures of the verification data, as disclosed above. However, in additional or alternative embodiments, the appended death certificate information 112 may be verified in other methods, including confirming certain verification data with relevant entities (e.g., government officials) associated with the appended death certificate information 112, for example. Since each node may receive a respective portion of the verification data, it should be appreciated the each node may be configured to verify the received portion of the verification data. However, collectively, the nodes of the distributed ledger 110 may verify all of the verification data associated with the appended death certificate information 112.

If the appended death certificate information 112 is determined to not be valid, the node may transmit a signal indicative that the appended death certificate information 112 is invalid, as indicated by block 160. As an example, the node may transmit a signal to other nodes of the distributed ledger 110 that the appended death certificate information 112 is invalid. In some embodiments, once a single node determines that the appended death certificate information 112 is invalid, other nodes may cease in verifying the appended death certificate information 112. However, in additional or alternative embodiments, certain nodes may continue to verify their portion of the verification data of the appended death certificate information 112. In this manner, certain portions of the verification data of the appended death certificate information 112 may be determined to be valid while other portions of the verification data of the appended death certificate information 112 may be determined to be invalid. When the appended death certificate information 112 is determined to be invalid, the appended death certificate information 112 may be marked (e.g., as contested). In particular embodiments, marked appended death certificate information 112 may be further analyzed to confirm that the appended death certificate information 112 is invalid. That is, other nodes of the distributed ledger 110 and/or entities outside of the distributed ledger 110 may be used to verify the appended death certificate information 112 before the appended death certificate information 112 is confirmed to be invalid. Moreover, in certain embodiments, if the appended death certificate information 112 is determined to be invalid, the node that sent the appended death certificate information 112 to the distributed ledger 110 may be flagged. As such, if the flagged node were to send appended death certificate information 112 in the future to the distributed ledger 110, other nodes would be aware that the flagged node has previously transmitted invalid appended death certificate information 112, which may affect how the other nodes verify information transmitted by the flagged node.

If the appended death certificate information 112 is determined to be valid, the node may transmit a signal indicative that the appended death certificate information 112 is valid, as shown in block 162. That is, the node may transmit a signal to other nodes of the distributed ledger 110 that their portion of the verification data is valid. Subsequently, the other nodes may continue to verify their portion of the verification data. In certain embodiments, once all nodes have transmitted a signal indicative that their respective portions of the verification data is valid, the entire appended death certificate information 112 may be indicated as valid. As a result, the appended death certificate information 112 may be added to the list of transactions (e.g., added as a block in the blockchain) of the distributed ledger 110 and the medical records 114 may update accordingly to include the updated information.

It should be understood that certain nodes may be capable of performing certain steps of the method 150. For example, if a node is an append-only type node, the node may be capable of performing the steps in blocks 152 and 154. If the node is a read-only type node, the node may be capable of performing the steps in blocks 156-162. If the node is capable of both append and read functions, the node may be capable of performing all steps in the method 150. Additionally, each node may perform actions of the method 150 via the user 104, the user device 102, the user application 106, or any combination thereof. In some embodiments, certain nodes of the distributed ledger 110 may perform certain steps together. As an example, multiple nodes of the distributed ledger 110 may, together, transmit a plurality of information to the distributed ledger 110. As such, the steps of the method 150 are not meant to illustrate steps performed by separate nodes independently. It should also be appreciated that there may be additional steps performed by the nodes that are not mentioned in the method 150, such as intermediate steps and/or actions unrelated to appending and/or reading functions. Each step in the method 150 may also be repeated. That is, certain steps may be performed several times throughout an iteration of the method 150 and additionally, it should be understood the method 150 may be performed several times, such as each time appended death certificate information 112 is added to the distributed ledger 110. Furthermore, it should be appreciated that the steps need not be performed in the exact order depicted in FIG. 2. For example, the steps of blocks 156-162 may be performed prior to the steps in blocks 152 and 154 such that the append functions are performed prior to the read functions.

Certain steps of the method 150 may also be performed differently based on the node performing the steps. That is, a node's capabilities and/or compliance with federal rules may affect how each node performs their functions. For example, a first node may adhere to a first set of rules and/or otherwise be limited of performing steps in a first manner. A second node may not adhere to any rules and thus, be capable of performing steps in any manner. Therefore, the first node and the second node may perform their functions in different manners. However, in some embodiments, all nodes may perform steps in a similar manner that may satisfy the functional capabilities and/or compliance with federal rules of all performing nodes. Thus, even though the second node may not adhere to any rules and thus, be capable of performing steps in any manner, the second node may perform the steps in the first manner such that the first node and the second node complete their functions in an approximately similar manner.

Figure 3:
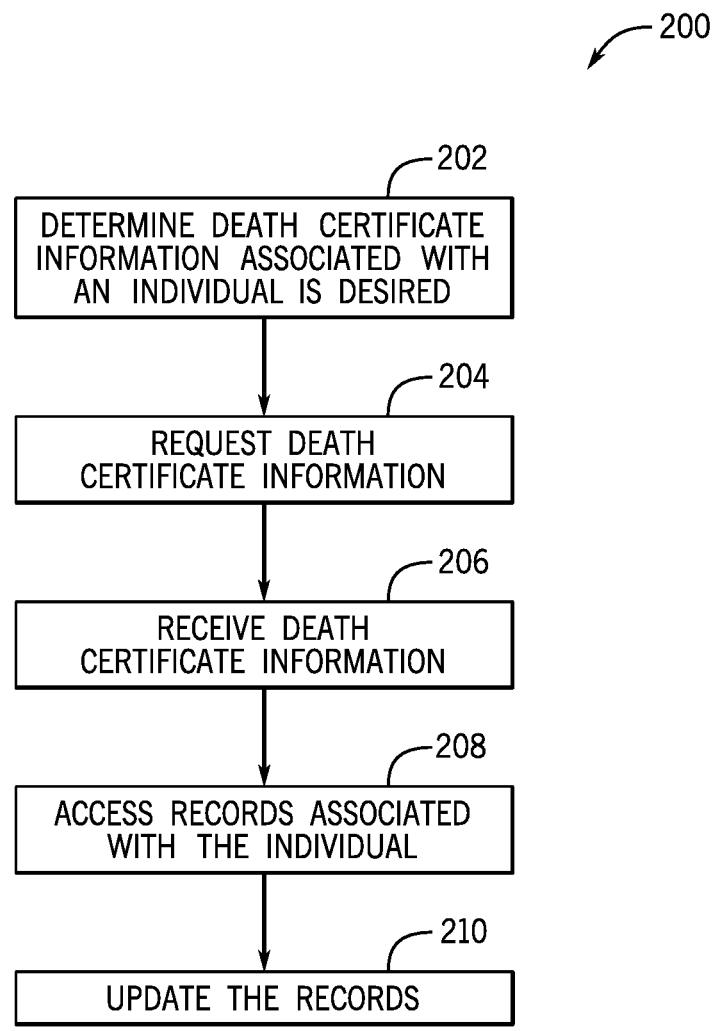
FIG. 3 illustrates a block diagram of updating individual records relating to death certificate information in accordance with embodiments described herein.

An entity, such as an entity outside of the distributed ledger 110 and/or otherwise not possessing a full record of the death certificate information 112 of the distributed ledger 110, may desire to receive death certificate information 112. FIG. 3 illustrates a block diagram of an embodiment of a method 200 for such an entity to act request for such death certificate information and then perform actions upon receiving the death certification information 112 (e.g., execute a smart contract). In block 202, the entity determines that death certificate information 112 is desired, where the death certificate information 112 is associated with an individual. For example, an entity, such as an employer, may determine that certain records are to be updated for an individual. The entity may determine that the records are associated with death certificate information 112 of the individual and thus, may desire to receive the death certificate information 112.

In block 204, the death certificate information 112 is requested by the entity. As an example, the entity may transmit a signal to the distributed ledger 110 requesting the death certificate information 112. In some embodiments, the distributed ledger 110 may be a public ledger that members of the general public may request information via providing identification information associated with the particular death certificate information 112, such as identification of an individual associated with the death certificate information 112, a date and/or time associated with the death certificate information 112, other content associated with the death certificate information 112, or any combination thereof. Thus, a member of the general public may then use such identification information to retrieve the particular death certificate information 112 desired. In additional or alternative embodiments, the entity may be associated with a node of the distributed ledger 110 and thus, may request the node directly for the death certificate and/or already possess a portion of the relevant death certificate information 112.

In block 206, the entity receives the death certificate information 112. The death certificate information 112 may include a full or partial record of the death certificate information 112. By way of example, the entity requesting the death certificate information 112 may be evaluated, such as by the nodes to determine if the entity is trustworthy. Based on the evaluation, a corresponding record of the death certificate information 112 may be given. For instance, a particular hospital may receive a full record of the death certificate information 112 to be able to update medical records 114 in full, while a utility company may receive a partial record of the death certificate information 112 to be able to update an account profile with relevant information from portions of the death certificate information 112. It should also be appreciated that certain entities may not be given any record of the death certificate information 112, such as if the particular entity is determined not to be trustworthy.

Upon receiving the death certificate information 112, the entity may determine particular records associated with the individual may be updated. Thus, in block 208, the entity may access records associated with the individual. The entity may determine the records to be updated are based off the received death certificate information 112. In an example, a bank may use the death certificate information 112 to determine if an account of the individual is to be updated based on the death certificate information 112.

In block 210, the records of the individual are updated. To continue the example, the bank may update a bank account of the individual to reflect information included in the death certificate information 112. In some embodiments, the records are updated based on a verification of the death certificate information 112. For example, if certain portions of the death certificate information 112 are valid but other portions of the death certificate information 112 are not valid, the records may be updated to reflect as such. It should be understood that the records may be updated as the death certificate information 112 is verified. That is, certain portions of the records may be updated when a first portion of the death certificate information is verified. Subsequently, other portions of the records may be updated when a second portion of the death certificate information is verified. Additionally, records of other individuals may be updated based on the death certificate information 112. For example, updating records of a first individual may result in identification of a second individual associated with the first individual. Records of the second individual may be analyzed to determine if such records are also to be updated.

As a result of updating the records, additional actions may be performed. That is, updating records of the individual may result in corresponding action relevant to the updated records. In one example, updating the bank account of the individual may result in the transfer of currency, titles, and/or other assets. In some embodiments, certain information associated with the death certificate information 112 may be saved, such as to a particular database associated with the entity, and may be used to process future death certificate information 112. For instance, the bank may store data associated with transaction histories of individuals whom the death certificate information 112 was requested about and may store data associated with the corresponding bank account records that were updated as a result of the requested death certificate information 112. The bank may use the data to determine certain parameters, such as a relationship between a transaction history and corresponding bank account records to be updated. Thus, updates of other bank account records in the future may be more accurate and more appropriate based on requested death certificate information 112. In some instances, such data may also be used to determine if a request for death certificate information 112 in the future is desired. For example, the bank may adjust the monetary threshold used to determine if a request for death certificate information 112 is to be sent to the distributed ledger 110. In certain embodiments, other information, such as other information on the medical records 114 of individuals, may also be used in conjunction with the death certificate information 112. In an additional example, medical records information, such as information associated with deoxyribonucleic acid (DNA) of an individual, may be stored upon receiving the death certificate information 112. The medical records information may be used to establish relationships between the death certificate information 112 and other information in the medical records 114, such as for use in actuarial science to predict future death certificate information 112 of individuals based on current medical records 114.

It should be appreciated that certain blocks of the method 200 may be performed automatically, such as via smart contracts. For example, determining that death certificate information 112 is desired may be performed via data (e.g., keyword) matching of current and/or received records or another analysis of information, which may result in determining that certain information is associated with an individual. In response to determining that death certificate information 112 of an individual is desired, the entity may automatically send a request for the death certificate information 112. Thus, a user device 102 (e.g., a computing device) may be configured to automatically perform blocks 202 and/or 204. To provide a scenario, a bank may determine a list of high monetary transactions are associated with hospital bills. If the monetary transactions surpass a monetary threshold, the bank may automatically request for death certificate information 112. In additional or alternative embodiments, the blocks 202 and/or 204 may also be performed in non-automatic manners, such as by manually reviewing medical records 114 to determine updated death certificate information 112 is desired. That is, a worker of the bank may be notified of recent transactions associated with an individual using the bank. The worker may then review the transactions and determine whether or not to request for death certificate information 112 from the distributed ledger 110. Additionally, blocks 208 and/or 210 may be performed automatically. As an example, the entity may analyze the death certificate information 112 to determine relevant records to be updated. The entity may then update the records accordingly and as a result, corresponding actions as a result of the updated records, such as a transfer of assets, are performed automatically.

It should be appreciated that steps not already mentioned, such as intermediate and/or additional steps, may be performed in the method 200. Moreover, in some embodiments, not all steps may be performed. That is, blocks 208 and/or 210 may not be performed if records are determined to not be changed based off the received death certificate information 112. It should also be understood that the steps of the method 200 may be performed by separate entities. As an example, an individual may request the death certificate information 112 and may forward the death certificate information 112 to a bank to update particular records. Further still, the method 200 may not be performed in the depicted order. For example, block 208 may be performed immediately after block 202 such that records associated with the individual are determined and accessed based on the information prior to receiving the death certificate information 112.

It should also be appreciated that certain steps of the method 150 and the method 200 may be combined. For example, a node may receive death certificate information, such as in block 156 of the method 150 and in block 206 of the method 200, and may proceed to verify the death certificate information as recited in block 158 of the method 150 and to update the records as recited in the block 210. Thus, certain nodes may be capable of performing steps of the method 150 and the method 200 for the same death certificate information 112.

Figure 4:
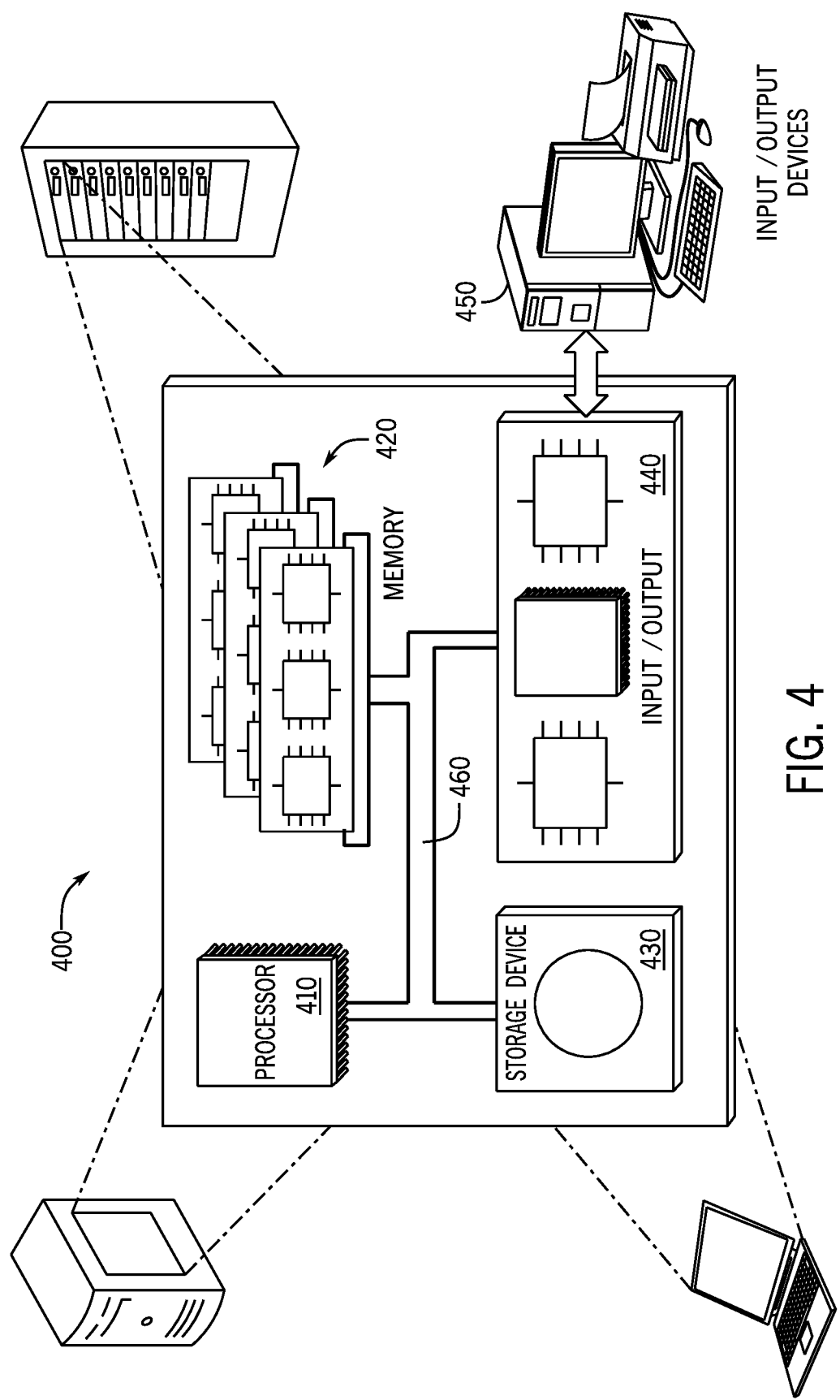
FIG. 4 illustrates a block diagram of a computing system that may be used in FIGS. 1-3, in accordance with embodiments described herein.

FIG. 4 illustrates a block diagram of a computing system that may be utilized in FIGS. 1-3, in accordance with embodiments described herein. The system 400 may be used for one or more of the operations described with respect to the various embodiments discussed herein. For example, the system 400 may be included, at least in part, in one or more of user device(s) 102, the distributed ledger system(s) 108, or other computing device(s) described herein. The system 400 may include one or more processors 410, a memory 420, one or more storage devices 430, and one or more input/output (I/O) devices 450 controllable through one or more I/O interfaces 440. The various components 410, 420, 430, 440, or 450 may be interconnected through at least one system bus 460, which may enable the transfer of data between the various modules and components of the system 400.

The processor(s) 410 may be configured to process instructions for execution within the system 400. The processor(s) 410 may include single-threaded processor(s), multi-threaded processor(s), or both. The processor(s) 410 may be configured to process instructions stored in the memory 420 or on the storage device(s) 430. The processor(s) 410 may include hardware-based processor(s) each including one or more cores. The processor(s) 410 may include general purpose processor(s), special purpose processor(s), or both.

The memory 420 may store information within the system 400. In certain embodiments, the memory 420 includes one or more computer-readable media. The memory 420 may include any suitable number of volatile memory units and/or non-volatile memory units. The memory 420 may include read-only memory, random access memory, or both. In some examples, the memory 420 may be employed as active or physical memory by one or more executing software modules.

The storage device(s) 430 may be configured to provide (e.g., persistent) mass storage for the system 400. In certain embodiments, the storage device(s) 430 may include one or more computer-readable media. For example, the storage device(s) 430 may include a floppy disk device, a hard disk device, an optical disk device, or a tape device. The storage device(s) 430 may include read-only memory, random access memory, or both. The storage device(s) 430 may include one or more of an internal hard drive, an external hard drive, or a removable drive.

One or both of the memory 420 or the storage device(s) 430 may include one or more computer-readable storage media (CRSM). The CRSM may include one or more of an electronic storage medium, a magnetic storage medium, an optical storage medium, a magneto-optical storage medium, a quantum storage medium, a mechanical computer storage medium, and so forth. The CRSM may provide storage of computer-readable instructions describing data structures, processes, applications, programs, other modules, or other data for the operation of the system 400. In certain embodiments, the CRSM may include a data store that provides storage of computer-readable instructions or other information in a non-transitory format. The CRSM may be incorporated into the system 400 or may be external with respect to the system 400. The CRSM may include read-only memory, random access memory, or both. One or more CRSM suitable for tangibly embodying computer program instructions and data may include any suitable type of non-volatile memory, including but not limited to: semiconductor memory devices, such as EPROM, EEPROM, and flash memory devices; magnetic disks such as internal hard disks and removable disks; magneto-optical disks; and CD-ROM and DVD-ROM disks. In some examples, the processor(s) 410 and the memory 420 may be supplemented by, or incorporated into, one or more application-specific integrated circuits (ASICs).

The system 400 may include one or more I/O devices 450. The I/O device(s) 450 may include one or more input devices such as a keyboard, a mouse, a pen, a game controller, a touch input device, an audio input device (e.g., a microphone), a gestural input device, a haptic input device, an image or video capture device (e.g., a camera), or other devices. In some examples, the I/O device(s) 450 may also include one or more output devices such as a display, LED(s), an audio output device (e.g., a speaker), a printer, a haptic output device, and so forth. The I/O device(s) 450 may be physically incorporated in one or more computing devices of the system 400, or may be external with respect to one or more computing devices of the system 400.

The system 400 may include one or more I/O interfaces 440 to enable components or modules of the system 400 to control, interface with, or otherwise communicate with the I/O device(s) 450. The I/O interface(s) 440 may enable information to be transferred in and/or out of the system 400, and/or between components of the system 400, through serial communication, parallel communication, and/or other types of communication. For example, the I/O interface(s) 440 may comply with a version of the RS-232 standard for serial ports, or with a version of the IEEE 1284 standard for parallel ports. As another example, the I/O interface(s) 440 may be configured to provide a connection over Universal Serial Bus (USB) or Ethernet. In some examples, the I/O interface(s) 440 may be configured to provide a serial connection that is compliant with a version of the IEEE 1394 standard.

The I/O interface(s) 440 may also include one or more network interfaces that enable communications between computing devices in the system 400, and/or between the system 400 and other network-connected computing systems. The network interface(s) may include one or more network interface controllers (NICs) or other types of transceiver devices configured to send and receive communications over one or more networks using any suitable network protocol.

Computing devices of the system 400 may communicate with one another, or with other computing devices, using one or more networks. Such networks may include public networks such as the internet, private networks such as an institutional or personal intranet, or any combination of private and public networks. The networks may include any suitable type of wired or wireless network, including but not limited to local area networks (LANs), wide area networks (WANs), wireless WANs (WWANs), wireless LANs (WLANs), mobile communications networks (e.g., 3G, 4G, Edge, etc.), and so forth. In certain embodiments, the communications between computing devices may be encrypted or otherwise secured. For example, communications may employ one or more public or private cryptographic keys, ciphers, digital certificates, or other credentials supported by a security protocol, such as any version of the Secure Sockets Layer (SSL) or the Transport Layer Security (TLS) protocol.

The system 400 may include one or more computing devices of any suitable type. The computing device(s) may include, but are not limited to: a personal computer, a smartphone, a tablet computer, a wearable computer, an implanted computer, a mobile gaming device, an electronic book reader, an automotive computer, a desktop computer, a laptop computer, a notebook computer, a game console, a home entertainment device, a network computer, a server computer, a mainframe computer, a distributed computing device (e.g., a cloud computing device), a microcomputer, a system on a chip (SoC), a system in a package (SiP), and so forth. Although examples herein may describe computing device(s) as physical device(s), certain embodiments are not so limited. In some examples, a computing device may include one or more of a virtual computing environment, a hypervisor, an emulation, or a virtual machine executing on one or more physical computing devices. In some examples, two or more computing devices may include a cluster, cloud, farm, or other grouping of multiple devices that coordinate operations to provide load balancing, failover support, parallel processing capabilities, shared storage resources, shared networking capabilities, or other aspects.

Certain embodiments and all of the functional operations described in this specification may be realized in digital electronic circuitry, or in computer software, firmware, or hardware, including the structures disclosed in this specification and their structural equivalents, or in combinations of one or more of them. Certain embodiments may be realized as one or more computer program products, such as one or more modules of computer program instructions encoded on a computer readable medium for execution by, or to control the operation of, data processing apparatus. The computer readable medium may be a machine-readable storage device, a machine-readable storage substrate, a memory device, a composition of matter effecting a machine-readable propagated signal, or a combination of one or more of them. The term "computing system" encompasses all apparatus, devices, and machines for processing data, including by way of example a programmable processor, a computer, or multiple processors or computers. The apparatus may include, in addition to hardware, code that creates an execution environment for the computer program in question, such as code that constitutes processor firmware, a protocol stack, a database management system, an operating system, or a combination of one or more of them. A propagated signal is an artificially generated signal, such as a machine-generated electrical, optical, or electromagnetic signal that is generated to encode information for transmission to suitable receiver apparatus.

A computer program (also known as a program, software, software application, script, or code) may be written in any appropriate form of programming language, including compiled or interpreted languages, and it may be deployed in any appropriate form, including as a standalone program or as a module, component, subroutine, or other unit suitable for use in a computing environment. A computer program does not necessarily correspond to a file in a file system. A program may be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program may be deployed to be executed on one computer or on multiple computers that are located at one site or distributed across multiple sites and interconnected by a communication network.

The processes and logic flows described in this specification may be performed by one or more programmable processors executing one or more computer programs to perform functions by operating on input data and generating output. The processes and logic flows may also be performed by, and apparatus may also be implemented as, special purpose logic circuitry, such as an FPGA (field programmable gate array) or an ASIC (application specific integrated circuit).

Processors suitable for the execution of a computer program include, by way of example, both general and special purpose microprocessors, and/or processor(s) of any appropriate kind of digital computer. Generally, a processor may receive instructions and data from a read only memory or a random access memory or both. Elements of a computer can include a processor for performing instructions and one or more memory devices for storing instructions and data. Generally, a computer may also include, or be operatively coupled to receive data from or transfer data to, or both, one or more mass storage devices for storing data, such as magnetic, magneto optical disks, or optical disks. However, a computer need not have such devices. Moreover, a computer may be embedded in another device, including a mobile telephone, a personal digital assistant (PDA), a mobile audio player, a Global Positioning System (GPS) receiver, to name just a few. Computer readable media suitable for storing computer program instructions and data include all forms of non-volatile memory, media and memory devices, including by way of example semiconductor memory devices, such as EPROM, EEPROM, and flash memory devices; magnetic disks, (e.g., internal hard disks or removable disks); magneto optical disks; and CD ROM and DVD-ROM disks. The processor and the memory may be supplemented by, or incorporated in, special purpose logic circuitry.

To provide for interaction with a user, certain embodiments may be realized on a computer having a display device, including a CRT (cathode ray tube) or LCD (liquid crystal display) monitor, for displaying information to the user and a keyboard and a pointing device (e.g., a mouse or a trackball), by which the user may provide input to the computer. Other kinds of devices may be used to provide for interaction with a user as well; for example, feedback provided to the user may be any appropriate form of sensory feedback, such as visual feedback, auditory feedback, or tactile feedback; and input from the user may be received in any appropriate form, including acoustic, speech, or tactile input.

Certain embodiments may be realized in a computing system that includes a back end component (e.g., as a data server), or that includes a middleware component (e.g., an application server), or that includes a front end component (e.g., a client computer having a graphical UI or a web browser) through which a user may interact with an implementation, or any appropriate combination of one or more such back end, middleware, or front end components. The components of the system may be interconnected by any appropriate form or medium of digital data communication (e.g., a communication network). Examples of communication networks include a local area network ("LAN") and a wide area network ("WAN") (e.g., the Internet).

The computing system may include clients and servers. A client and server are generally remote from each other and typically interact through a communication network. The relationship of client and server arises by virtue of computer programs running on the respective computers and having a client-server relationship to each other.

While only certain features of disclosed embodiments have been illustrated and described herein, many modifications and changes will occur to those skilled in the art. It is, therefore, to be understood that the appended claims are intended to cover all such modifications and changes as fall within the true spirit of the present disclosure.

The techniques presented and claimed herein are referenced and applied to material objects and concrete examples of a practical nature that demonstrably improve the present technical field and, as such, are not abstract, intangible or purely theoretical. Further, if any claims appended to the end of this specification contain one or more elements designated as "means for [perform]ing [a function] . . . " or "step for [perform]ing [a function] . . . ", it is intended that such elements are to be interpreted under 35 U.S.C. 112(f). However, for any claims containing elements designated in any other manner, it is intended that such elements are not to be interpreted under 35 U.S.C. 112(f).

The invention claimed is:

1. A system comprising:
at least one processor;
at least one memory communicatively coupled to the at least one processor, the at least one memory storing instructions that, when executed by the at least one processor, are configured to cause the at least one processor to:
receive a block of first death certificate information from a node of a distributed ledger system, wherein the first death certificate information is associated with an individual, and
the first death certificate information comprises a portion of a death certificate information set;
determine, based at least in part on the death certificate information, a record to be updated, wherein the record is associated with the individual; and
update the record to generate an updated record;
at least one additional processor; and
at least one additional memory communicatively coupled to the at least one additional processor, the at least one additional memory storing other instructions that, when executed by the at least one additional processor, are configured to cause the at least one additional processor to:
receive second death certificate information from an additional node of the distributed ledger system, wherein the second death certificate information comprises another portion of the death certificate information set, and the second death certificate information comprises verification data; and
verify that the second death certificate information is valid based at least in part on the verification data.

2. The system of claim 1, wherein the instructions, when executed by the at least one processor, are configured to cause the at least one processor to receive the first death certificate information associated with the individual based at least in part on a matching of data in the first death certificate information to data associated with the individual from a plurality of data associated with individuals being monitored in the distributed ledger system.

3. The system of claim 2, wherein the instructions, when executed by the at least one processor, are configured to cause the at least one processor to request the first death certificate information from the distributed ledger system upon receiving a notification associated with the individual.

4. The system of claim 3, wherein the instructions, when executed by the at least one processor, are configured to cause the at least one processor to request the first death certificate information via providing identification information associated with the first death certificate information.

5. The system of claim 1, wherein the instructions, when executed by the at least one processor, are configured to cause the at least one processor to update the record based at least in part on the first death certificate information.

6. The system of claim 1, wherein the distributed ledger system is a public distributed ledger system, wherein the node is configured to transmit third death certificate information to the public distributed ledger system.

7. The system of claim 1, wherein the instructions, when executed by the at least one processor, are configured to cause the at least one processor to save the death certificate information to the at least one memory.

8. The system of claim 1, wherein the instructions, when executed by the at least one processor, are configured to cause the at least one processor to:
determine, based at least in part on the updated record, an additional record to be updated, wherein the additional record is associated with an additional individual; and
update the additional record to generate an updated additional record.

9. A system comprising:
a node of a plurality of nodes of a distributed ledger system, the node comprising:
at least one processor; and
at least one memory communicatively coupled to the at least one processor, the at least one memory storing instructions that, when executed by the at least one processor, are configured to cause the at least one processor to:
receive first death certificate information from another node of the plurality of nodes, wherein the first death certificate information comprises verification data, and the first death certificate information comprises a portion of a death certificate information set;
verify that the first death certificate information is valid based at least in part on the verification data;
access a blockchain associated with an individual upon verifying that the first death certificate information is valid; and
add at least one block to the blockchain based at least in part on validation of the first death certificate information to immutably store the first death certificate information as part of the blockchain;
an additional node of the plurality of nodes of the distributed ledger system, the additional node comprising:
at least one other processor; and
at least one other memory communicatively coupled to the at least one other processor, the at least one other memory storing other instructions that, when executed by the at least one other processor, are configured to cause the at least one other processor to:
  receive second death certificate information from the another node of the plurality of nodes, wherein the second death certificate information comprises another portion of the death certificate set, and the second death certificate information comprises another verification data; and
  verify that the second death certificate information is valid based at least in part on the another verification data.

10. The system of claim 9, wherein the distributed ledger system is a private distributed ledger system, wherein each node of the plurality of nodes of the private distributed ledger system comprises a computing device, and wherein each computing device is configured to receive the first death certificate information.

11. The system of claim 9, wherein the instructions, when executed by the at least one processor, are configured to cause the at least one processor to verify the first death certificate information via verifying signature data associated with the verification data.

12. The system of claim 9, wherein the instructions, when executed by the at least one processor, are configured to cause the at least one processor to transmit a signal to other nodes of the plurality of nodes upon verifying that the first death certificate information is valid to cause adding the at least one block to the blockchain stored in the other nodes.

13. The system of claim 9, wherein the instructions, when executed by the at least one processor, are configured to cause the at least one processor to transmit a signal to other nodes of the plurality of nodes upon determining that the first death certificate information is invalid, and wherein the instructions, when executed by the at least one processor, are configured to cause the at least one processor to flag other nodes of the plurality of nodes upon determining that the first death certificate information is invalid, wherein the at least one block is not added to the blockchain upon determining that the first death certificate information is invalid.

14. The system of claim 9, wherein the other instructions, when executed by the at least one other processor, are configured to cause the at least one other processor to transmit a signal to the node upon verifying that the second death certificate information is valid, wherein, upon receiving the signal, the instructions, when executed by the at least one processor, are configured to cause the at least one processor to:
  access a record associated with the individual;
  determine that the record of the individual comprises updates triggered by the second death certificate information; and
  update the additional record according to the updates.

15. A system comprising:
  at least one processor;
  at least one memory communicatively coupled to the at least one processor, the at least one memory storing instructions that, when executed by the at least one processor, are configured to cause the at least one processor to:
    receive a blockchain from a first node of a distributed ledger system, wherein the blockchain comprises at least one block of first death certificate information, wherein the first death certificate information comprises a portion of a death certificate information set;
    identify that the first death certificate information is associated with an individual;
    append the blockchain upon identifying that the first death certificate information is associated with the individual to generate an appended blockchain; and
    determine a record to be updated based at least in part on the first death certificate information, wherein the record is associated with the individual;
  at least one additional processor; and
  at least one additional memory communicatively coupled to the at least one additional processor, the at least one additional memory storing other instructions that, when executed by the at least one additional processor, are configured to cause the at least one additional processor to:
    receive the blockchain from a second node of the distributed ledger system, wherein the blockchain comprises at least one additional block of second death certificate information, wherein the second death certificate information comprises an additional portion of the death certificate information set, and the second death certificate information comprises verification data; and
    verify that the second death certificate information is valid based at least in part on the verification data.

16. The system of claim 15, comprising:
  at least one other processor; and
  at least one other memory communicatively coupled to the at least one other processor, the at least one other memory storing other instructions that, when executed by the at least one other processor, are configured to cause the at least one other processor to:
    receive the appended blockchain from the first node, wherein the appended blockchain comprises verification data; and
    verify that the appended blockchain is valid based at least in part on the additional verification data.

17. The system of claim 15, wherein the instructions, when executed by the at least one processor, are configured to cause the at least one processor to append the blockchain via adding information to the first death certificate information, wherein the information comprises medical information associated with the individual.

18. The system of claim 15, wherein the at least one processor and the at least one memory are associated with a computing device, wherein the computing device is associated with a third node of the distributed ledger system.

19. The system of claim 15, wherein the instructions, when executed by the at least one processor, are configured to cause the at least one processor to receive a request for the blockchain and to distribute the blockchain upon receiving the request for the blockchain.

* * * * *